United States Patent [19]
Cholli et al.

[11] Patent Number: 5,985,120
[45] Date of Patent: Nov. 16, 1999

[54] RAPID ANALYSIS OF ANALYTE SOLUTIONS

[75] Inventors: Ashok L. Cholli, Chelmsford, Mass.; Eugene F. Barry, Nashua, N.H.; Sukant K. Tripathy, Acton; Jayant Kumar, Westford, both of Mass.

[73] Assignee: University of Massachusetts, Boston, Mass.

[21] Appl. No.: 08/873,473

[22] Filed: Jun. 12, 1997

[51] Int. Cl.$^6$ ................................................. G01N 27/26
[52] U.S. Cl. .................... 204/452; 210/656; 204/603; 702/25
[58] Field of Search ............................. 210/656; 95/25, 95/82; 364/550; 204/451, 452, 456, 461, 601, 603, 606, 612; 702/23, 24, 25, 32

[56] References Cited

U.S. PATENT DOCUMENTS

| | | | |
|---|---|---|---|
| 4,807,148 | 2/1989 | Lacey | 702/32 |
| 4,837,726 | 6/1989 | Hunkapiller | 702/32 |
| 4,909,919 | 3/1990 | Morris et al. | 204/603 |
| 5,098,536 | 3/1992 | Anderson | 204/452 |
| 5,242,602 | 9/1993 | Richardson et al. | 210/745 |
| 5,273,632 | 12/1993 | Stockham et al. | 204/450 |
| 5,296,116 | 3/1994 | Guttman | 204/605 |
| 5,395,502 | 3/1995 | Pawliszyn | 204/603 |
| 5,630,924 | 5/1997 | Fuchs et al. | 204/601 |
| 5,748,491 | 5/1998 | Allison et al. | 1/1 |

FOREIGN PATENT DOCUMENTS

| | | |
|---|---|---|
| 0 558 233 A1 | 9/1993 | European Pat. Off. . |
| WO 93/21592 | 10/1993 | WIPO . |

OTHER PUBLICATIONS

Lilley et al. ("Drug identification in biological matrixes using capillary electrophoresis and chemometric software", J. Chromatogr., B: Biomed. Appl., 1996, 683(1), 67–76), Aug. 1996.

Aries, Rupert E., et al., *Chemistry in Britain*, 821–824 (1991).
Bicchi, Carlo P., et al., *J. Agric. Food Chem.*, 43:1549–1555 (1995).
Cserhàti, Tibor, et al., *Journal of Pharmaceutical & Biochemical Analysis*, 9(9):685–691 (1991).
Cserhàti, Tibor, et al., *Journal of Pharmaceutical & Biochemical Analysis*, 10(10–12):1033–1039 (1992).
Forgàcs, Esther, *Journal of Pharmaceutical & Biomedical Analysis*, 13(4/5):525–532 (1995).
Jellum, E., et al., *Journal of Pharmaceutical & Biomedical Analysis*, 9(8):663–669 (1991).
Khrapko, K., et al., *Nucleic Acids Research*, 22(1):364–369 (1994).
Koepf, Sandy M., et al., *Journal of Cellular Biochemistry*, Abstract No. D 403, 18A:202 (1994).
Liang, Yi–zeng, et al., *Journal of Chromatography*, A.662:113–122 (1994).
Lindberg, Walter, et al., *Anal. Chem.*, 58:299–303 (1986).
Malmquist, Gunnar, et al., *Journal of Chromatography*, A.687:71–88 (1994).
Zhang, Peixun, et al., *Analytica Chimica Acta.*, 258:1–10 (1992).

*Primary Examiner*—Terrence R. Till
*Assistant Examiner*—Alex Noguerda
*Attorney, Agent, or Firm*—Fish & Richardson P.C.

[57] ABSTRACT

The separation profile results of capillary zone electrophoresis can be analyzed very rapidly, e.g., in 45 seconds or less, if the results are analyzed using a successive subtracting procedure to establish the separation profile as a function of time and projecting this separation profile forward in time to quantitatively analyze the separate species in the profile. The projection step can be accomplished using an algorithm along with or without Fourier transform (FT) techniques and the quantitative analysis can be carried out using principle component regression analysis (PCA) or suitable calibration procedures.

25 Claims, 11 Drawing Sheets

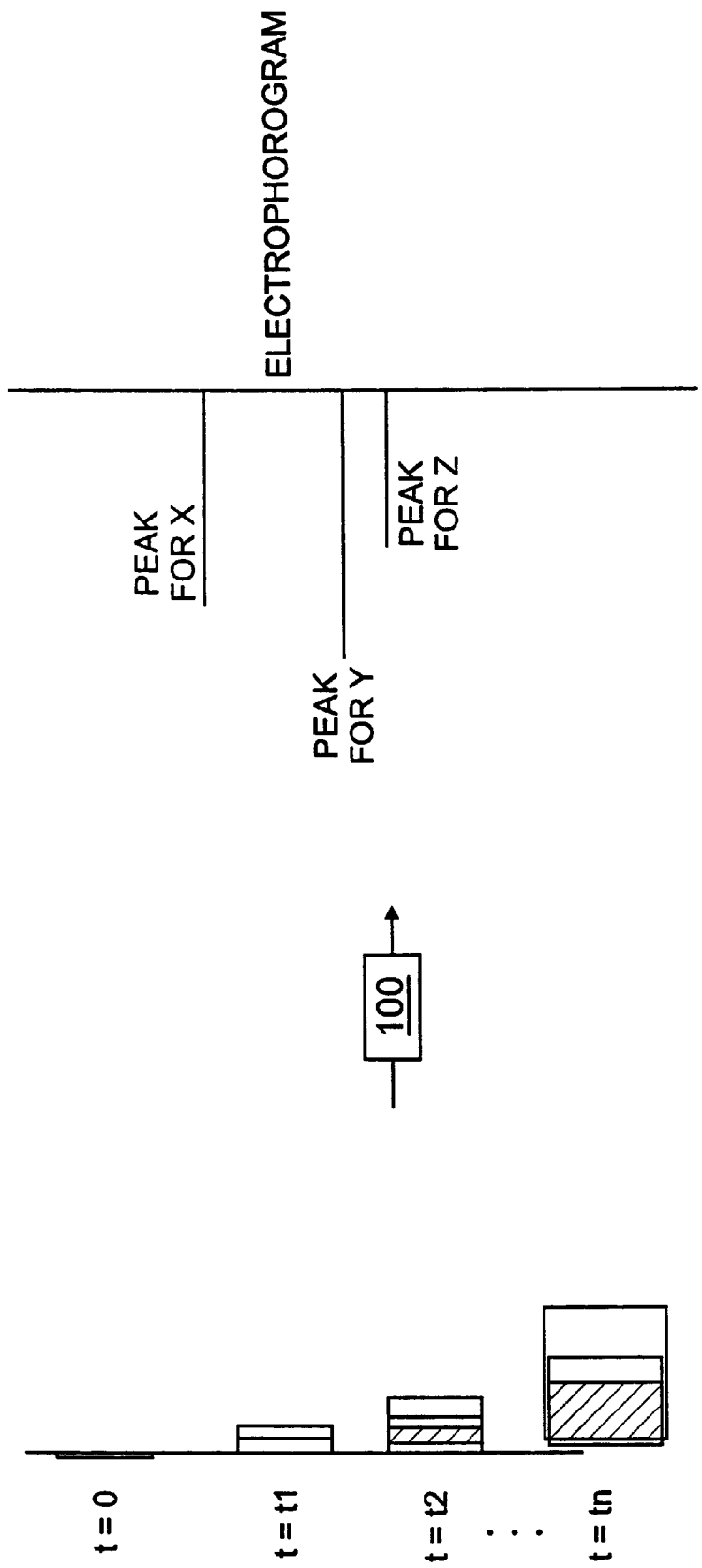

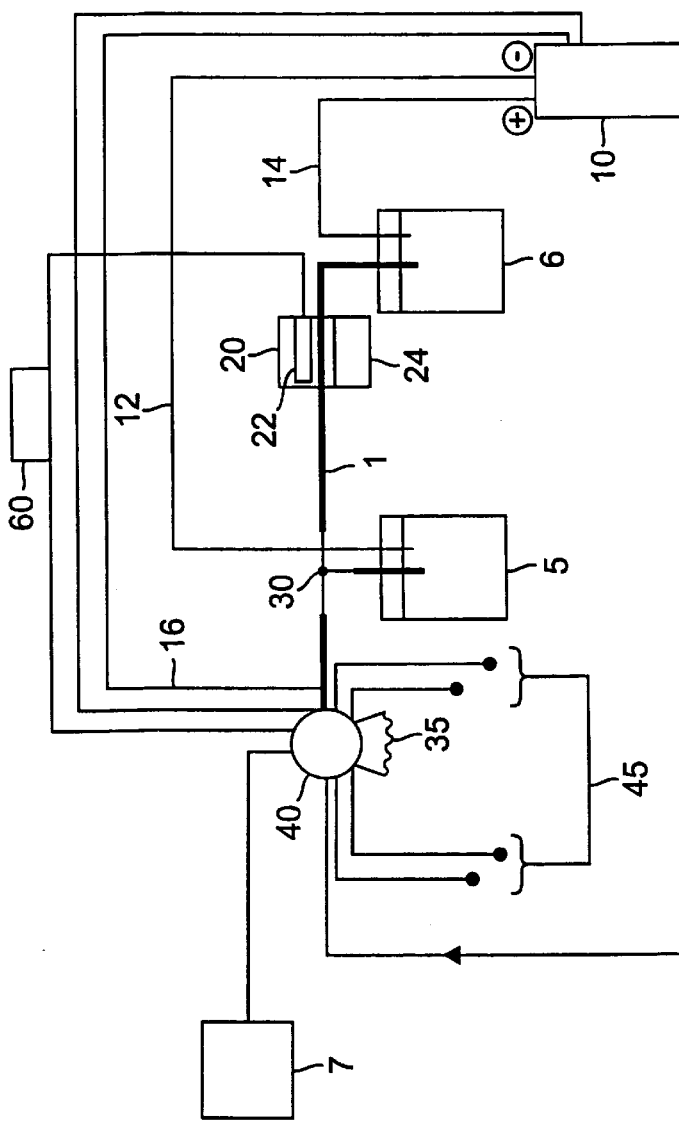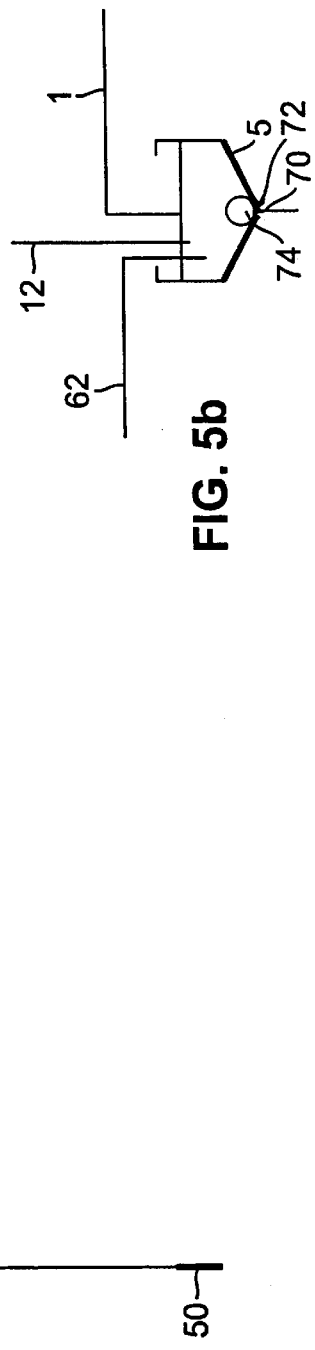
FIG. 5a
FIG. 5b

RAPID ANALYSIS OF ANALYTE SOLUTIONS

BACKGROUND OF THE INVENTION

The invention relates to the rapid analysis of analyte solutions.

Chromatographic methods can be used to separate components in a sample mixture to determine identity and quantity of each component in the sample. Chromatographic and electrophoretic techniques that are typically used to analyze complex mixtures include gas chromatography, liquid chromatography, high performance liquid chromatography, ion-exchange chromatography, gel filtration chromatography, thin layer chromatography, electrophoresis, and capillary electrophoresis. These techniques are relatively time consuming, since they require some degree of separation of the components in order to identify and quantify them.

Complex chromatographic patterns have been analyzed using principal component regression analysis, as described, for example, in Jellum, et al. Journal of Pharm. Biomed. Analysis, 9(8):663–669 (1991). Other processing techniques have been used to enhance the signal-to-noise ratio in chromatograms. See, for example, Anderson, U.S. Pat. No. 5,098,536.

SUMMARY OF THE INVENTION

The invention is based on the discovery that the separation profile of ions in analyte solutions using separation technology can be analyzed very rapidly, e.g., in 45 seconds or less, by analyzing a separating profile using a successive subtracting procedure to establish the separation profile as a function of time and projecting this profile forward in time to quantitatively analyze the separated species in the profile. The projection step can be accomplished by applying Fourier transform (FT) techniques to an early stage of an electropherogram created as a result of an applied electric field across the capillary whose ends are immersed in a suitable buffer and the quantitative analysis can be carried out using principle component regression analysis (PCA). This analysis method enables the use of new rapid sensors for identifying and quantifying different components of complex analyte solutions.

For example, a capillary zone electrophoresis (CZE) sensor that analyzes data based on this method can be used in quality control analysis of, for example, aqueous-based extracts of solids, liquids, or gasses. In particular, the amounts of specific components, e.g., contaminants, in water are determined rapidly, typically in less than about thirty seconds. The sensor can detect a wide range of contaminant concentrations. Particular contaminants of interest in water include chloride, nitrite, sulfate, nitrate, fluoride, phosphate, and cyanide anions, as well as potassium, calcium, magnesium, cadmium, zinc, and lead cations.

In one aspect, the invention features a method of measuring concentrations of individual species in a sample. A sample containing a plurality of individual species is introduced into a capillary. The sample is moved through the capillary for an analysis time to begin separating the individual species in the sample. A series of profiles of the plurality of individual species are measured along an analysis length of the capillary at incremental sampling times (e.g., measurements taken at intervals between 1 ms and 1000 ms apart) with the detector during the analysis time to provide a data set. Each profile is subtracted from the profile measured one sampling time earlier in the data set to obtain a time dependent data set. The time dependent data set is projected to obtain a separated concentration profile. The separated concentration profile is analyzed to determine concentrations of individual species in the sample.

In another aspect, the invention features a method of measuring concentrations of individual species in a sample. The sample is introduced into a capillary column, moved through the column, and a series of profiles is measured to provide a data set. A Fourier transform is applied to the data set to obtain a separated concentration profile which is analyzed by using principle component regression to determine concentrations of individual species in the sample. In embodiments, each profile can be subtracted from the profile measured one sampling time earlier in the data set to obtain a time dependent data set.

A time reference shift can be applied to each profile in the data set prior to the subtracting step. The time dependent data set can be projected, for example, by applying a Fourier transform to the time dependent data set. The separated concentration profile can be analyzed using principle component regression.

The capillary can be associated with a detector arranged to detect each of the individual species in the capillary along an analysis length of the capillary. The capillary can have an inner diameter of between 25 and 100 micrometers and can have an effective length of less than 20 cm.

The detector can be positioned adjacent to the capillary. The detector can be an absorbance measuring detection device or an array that detects species along the analysis length of the capillary. The detector can move along the analysis length of the capillary. The detector can detect species along the effective length of the capillary. Alternatively, the detector position can be variable relative to the separation profile in the capillary.

The sample can be moved through the capillary by applying a voltage across a length of the capillary. In certain embodiments, the applied voltage can be varied. The voltage can be applied, for example, for between 1 and 45 seconds.

In another aspect, the invention features a system of measuring concentrations of individual species in a sample. The system includes a capillary column, a detector arranged to detect each of the individual species in the capillary along an analysis length of the column at incremental sampling times during the analysis time to provide a data set, and an analyzer for analyzing the data set to determine concentrations of individual species in the sample. The system can include a two reservoir system; containing a buffer solution and a power supply that applies a voltage along the length of the capillary. Each capillary end is inserted into each of the two reservoirs.

In another aspect, the invention features a sensor for measuring species concentrations in a liquid sample. The sensor includes two buffer reservoirs, a capillary, a detector, a power supply, and a processor. Each of the reservoirs is capable of containing buffer solution. The capillary connects the reservoirs. The detector is positioned on the capillary at a distance (e.g., the analysis length) from the end of the capillary at one of the reservoirs. The power supply applies a voltage along the length of the capillary. The processor is connected to the detector and identifies individual species in the liquid sample by difference and projection, principle component regression, or Fourier transform analysis. The liquid sample can be substantially aqueous.

In another aspect, the invention features an injection reservoir for capillary zone electrophoresis. The injection reservoir includes a bottom, an orifice located at the bottom of the reservoir, and a plunger having an open position and a closed position. The plunger forms a seal with the orifice in the closed position and allows fluid to flow through the orifice in the open position. The plunger can include a sealing ball capable of forming a seal with the orifice when in the closed position.

The "analysis length" of a column is the length of the column along which the detector identifies species in the column.

A "cationic component" is a positive ion present in the sample. Cationic components include, for example, ammonium, potassium, sodium, calcium, and magnesium.

An "anionic component" is a negative ion present in sample. Anionic components include, for example, nitrate, nitrite, phosphate, and phosphite.

A "chelating agent" is a molecule that binds to a metal ion through more than one atom. Some examples of chelating agents include polyamines such as diamines and tetraamines, polyethers, and macrocyclic heterocycles such as crown ethers (e.g., 18-crown-6 ether) and cryptates.

A "cation buffer solution" is a buffer solution used to analyze cationic components in a sample by CZE.

An "anion buffer solution" is a buffer solution used to analyze anionic components in a sample by CZE.

"Projecting" is a method of moving a separation profile forward in time to quantitatively analyze the separate species in the profile. A data set containing profiles taken at incremental sampling time periods contains encoded information that is systematically extracted for each component by subtracting each profile in time in the data set from the preceding profile in time to give the relative change of position of the component as a function of time ($\Delta$; the time dependent data set). The time dependent data set represents the changing position of the component as the sample mixture passes through the capillary and can be used to forward project the peak positions for each component in the sample, as if the components were allowed to separate completely. The projection is accomplished by multiplying the time dependent data set by a value of time until each individual species profile can be distinguished from the other.

The new methods and systems provide the following advantages. In particular, the methods allow for quantitative determination of the concentrations of individual components in a sample by separation methods without completely separating the components. This allows samples to be analyzed rapidly. For example, the CZE analysis time can be reduced to less than a minute from the typical analysis times of about 20 to 30 minutes.

The new methods allow the total length of a separation capillary column to be reduced. For example, in CZE, the length of the capillary column can be shortened to a few centimeters from the usual length of about 100 cm, dramatically reducing the voltage applied across the length of the capillary.

Thus, the new methods facilitate the miniaturization of sensor devices. These sensors can be used as on-line monitoring devices for detecting contaminants in near real time. As an example, the pollutants in drinking, well, and industrial waste water can easily be monitored on a near real-time basis for EPA compliance. The new miniature sensors can be used as for quality control applications. Most importantly, they can be used to identify compounds in the synthesis and production of chemicals, and quality assurance programs. Advantages of using the methods with a CZE sensor for analysis of water samples include the high separation efficiency of the technique, i.e., the number of theoretical plates (N) is greater than $10^5$ to $10^6$, short analysis time (less than thirty seconds) for determining levels of contaminants in the water, and small sample volumes (1 to 50 nL) needed for accurate analysis. Together, these advantages allow anionic or cationic contaminants in water to be determined in a single rapid analysis run.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 3B is a graph showing the absorbance response of the detector of FIG. 3A. FIG. 3C is an electropherogram (chromatogram) resulting from the graph of FIG. 3B.

FIG. 5A is a schematic diagram depicting a CZE sensor for analyzing an aqueous sample.

FIG. 5B is a schematic diagram depicting a reservoir with a drain valve.

DETAILED DESCRIPTION

The invention covers methods and systems for rapid analysis of mixtures of components in samples. For example, the concentrations of anionic or cationic contaminants in water can be determined in less than thirty seconds using the method applied to capillary zone electrophoresis (CZE), thus allowing analysis of a water sample to occur almost immediately. The method significantly reduces the analysis time. The method can be applied to other separation methods that utilize an absorbance detector, such as liquid chromatography (including HPLC), thin layer chromatography, and electrophoresis.

Methods of Detection and Quantitation

Figure 1A:
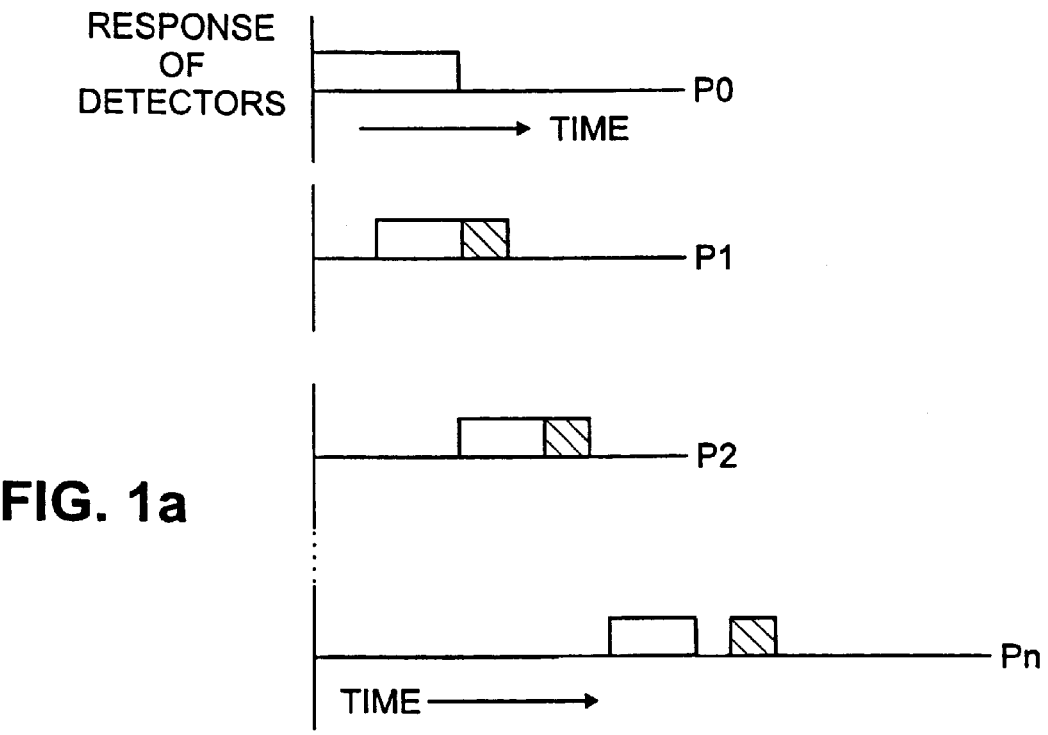
FIGS. 1A to 1D are schematic diagrams depicting four steps of the new subtraction method used to process data collected using an absorbance detector for analyzing a single component profile.
Figure 1B:
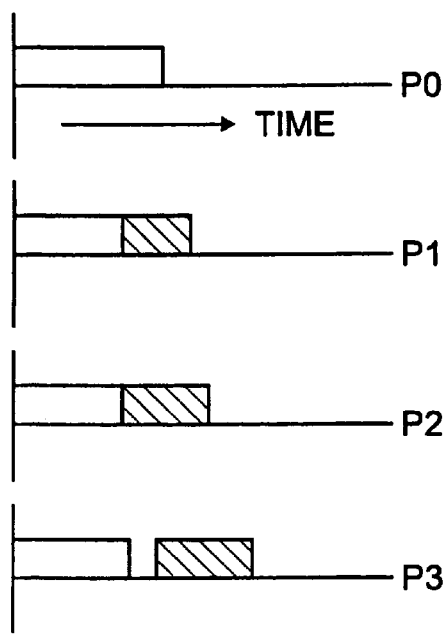

The methods involve monitoring the simultaneous response of all species immediately after a sample begins moving through a capillary. For example, in a CZE sensor, the species in the sample begin moving once subjected to an electric field. The new methods are based on the discovery that it is not necessary to observe actual physical separation of each component profile in the sample. The process is summarized in FIGS. 1A to 1D and 2A to 2B. Profiles are collected from the detector at incremental sampling times during the analysis time to provide the data set (P0, P1, . . ., Pn) shown in FIG. 1A. The data set can be shifted to a suitable time reference, as shown in FIG. 1B to facilitate comparison of the profiles. For example, in CZE the time reference can be the time when the high voltage field is turned on (t=0 seconds).

Figure 1C:
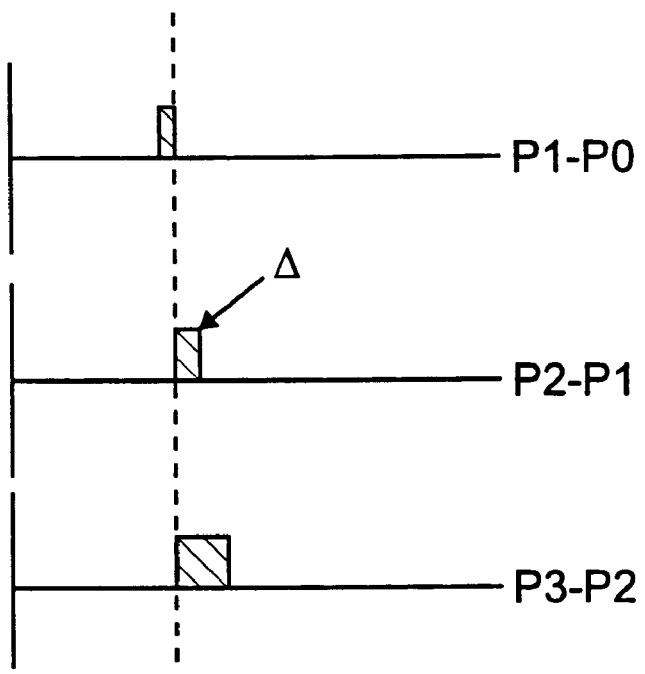
Figure 1D:
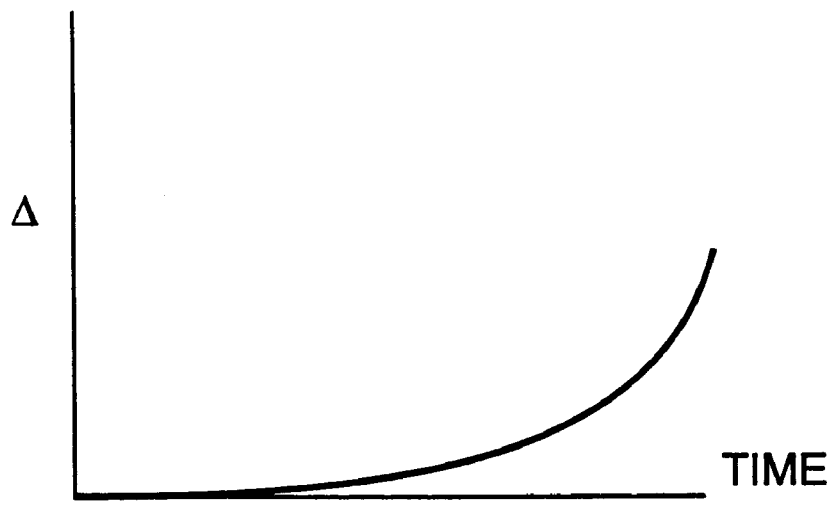

The relative position of the profile of each component is encoded as a function of time within the data set. Each component responds differently to the separation conditions. The relative positions of the components are established early in the run and do not change. For example, once species X is ahead of species Y, this migration order will not change under the actual separation conditions. A combination of commercially available software can be used for data acquisition and data processing. For example, suitable software is available from Galactic Industries Corporation, Salem, NH, part number Grams/386 GCRHOM-2, National Instruments, Austin, TX, part number Labview software, or MathSoft, Cambridge, MA, part number MathCad plus 6.0. This encoded information is systematically extracted for the profile of each component by subtracting each successive profile in the data set from the preceding profile to give the relative change of position of the component as a function of time (A; the time dependent data set), as shown in FIG. 1C. Referring to FIG. 1D, the time dependent data set represents the changing position of the component as the sample mixture passes through the capillary.

Figure 2B:
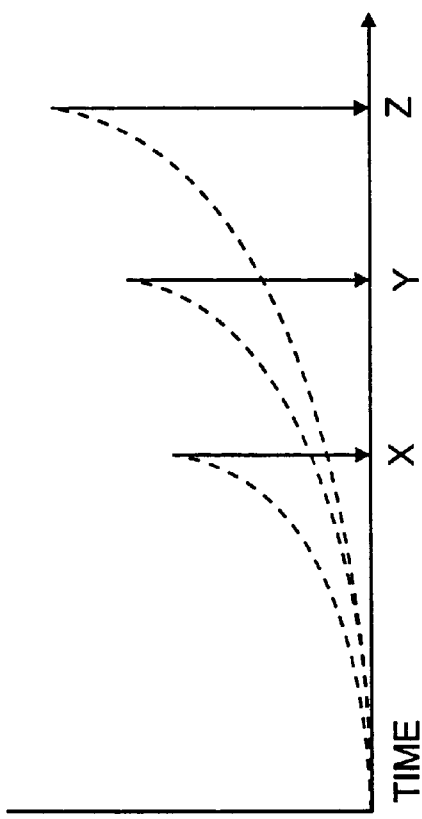
FIG. 2A and 2B are diagrams depicting the forward projection of a data set of profiles.
Figure 2A:
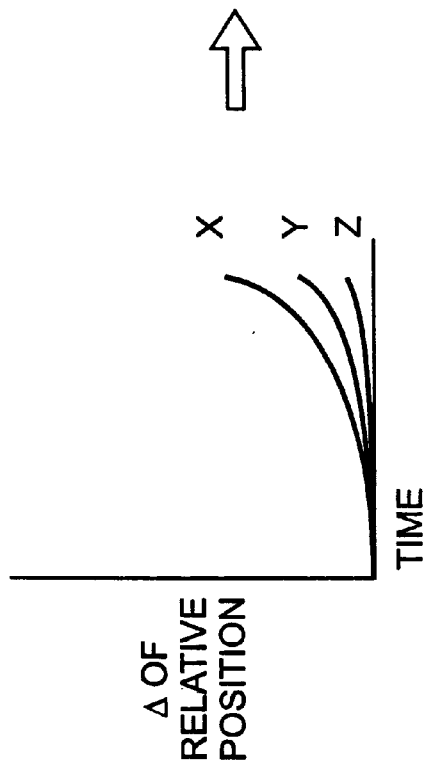

The time dependent data set (e.g., shown in FIG. 1D for one component) is then used to forward project the peak positions for each component in the sample. Referring to FIGS. 2A to 2B, the processed data can be forward projected to show the position of the peaks if the components were allowed to separate completely, representing a separated concentration profile. FIG. 2A shows the initial response of Δ versus time. FIG. 2B shows the projected response of Δ versus time. In FIG. 2B, the vertical downward arrow times represent the actual separation. The initial curve of Δ versus time can be used to project the position of the peak of the component if allowed to separate completely. A correlation can be established for a given component between Δ versus time and actual separation of the component. The resulting separated concentration profile is quantitatively analyzed, for example, using principle component regression analysis or any other suitable calibration method (e.g., least squares fitting, curve fitting, or partial least squares fitting). The processing of the data can be carried out, for example, using the software described above.

Figure 3A:
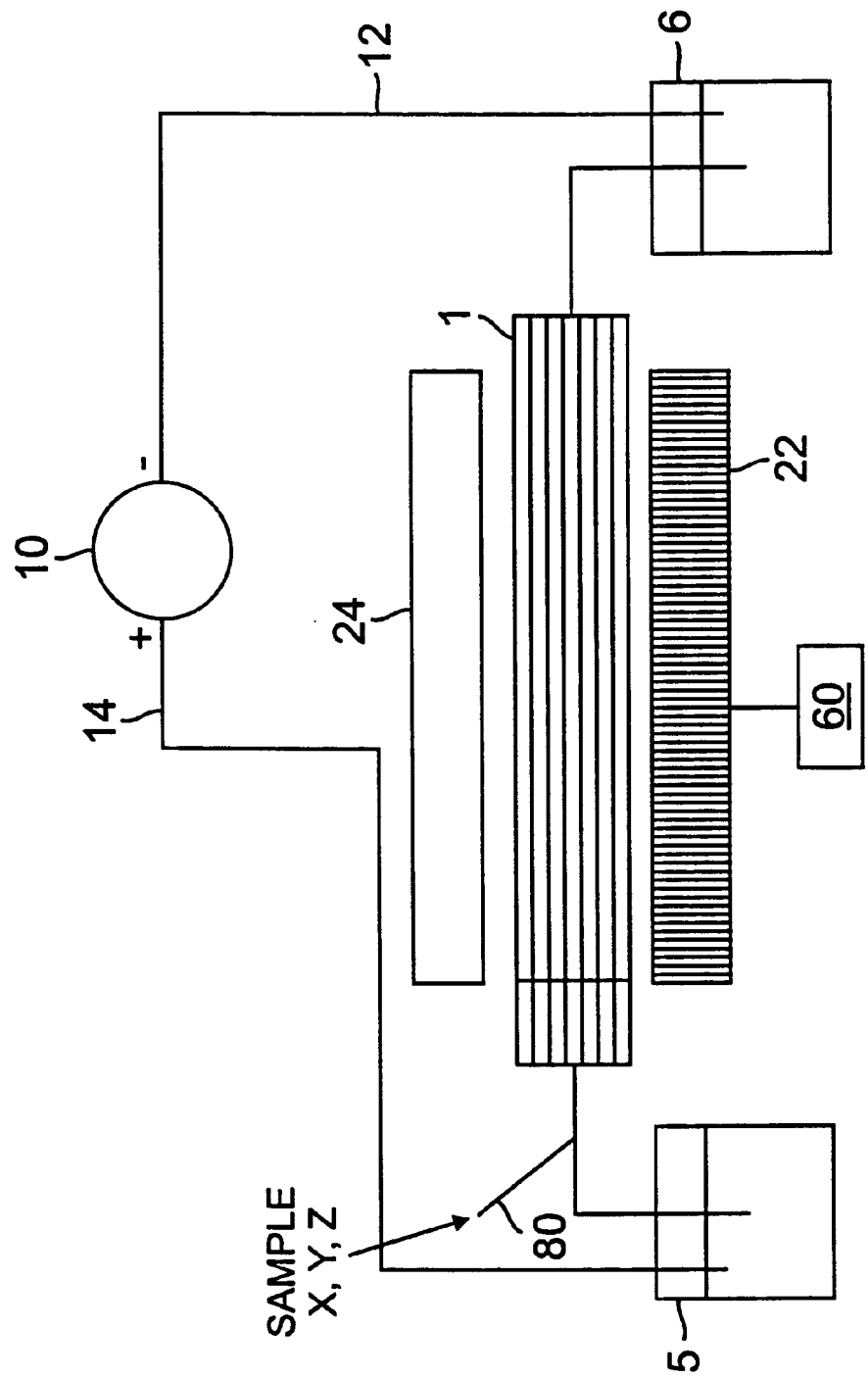
FIG. 3A is a schematic diagram depicting a CZE sensor having a diode array detector.

The method of processing the time-dependent chromatogram is outlined in FIGS. 3A to 3C. Referring to FIG. 3A, a CZE sensor features fused silica capillary 1 that is filled with a buffer solution. The capillary serves, at least in part, as a detection window, the dimensions of which depend on the detector used in the sensor. The ends of capillary 1 are immersed in a buffer solution contained in buffer reservoirs 5 and 6. Initially, the fluid levels (i.e., buffer solutions) in reservoir 5 and reservoir 6 are equal. The sample (containing components x, y, and z) is injected via capillary 80 by, for example, electrokinetic injection. A voltage is applied across the length of capillary 1 using power supply 10 via conductors 12 and 14.

Detector 22 is an array detector which is illuminated by light source 24. The absorbance detector (e.g., diode array detector) monitors the change in absorbance along an analysis length of the capillary. The detector can be, for example, a photodiode detector (UV enhanced) for photometric indirect detection, available from UDT Sensors, Hawthorne, CA, model number UDT-455UV/LN, or Hamamatsu Photonics, Bridgewater, NJ, model number, S1406. Alternatively, the detector can be, for example, a diode array detector, such as a CCD array detector for the 190–1080 nm spectral range, available from Princeton Instruments, Trenton, NJ, including Dual Diode Array Detector, Model number RL1024RAQ with dual 1024 diodes, Model Number RL1024SAQ with dual 1024 diodes, or CCD Detector, Model Number RTE/CCD-128. The detector can include filters for selected wavelength ranges (e.g., 254 nm, or 214 nm with 10 nm band width pass), available from Optical Corporation of America, Marlborough, MA, model number MC-254-R. The detector can include gratings or holographic gratings to selected other spectral regions and bands, such as holographic gratings for 160 nm to 800 nm, available from Acton Research Corporation, Acton, MA, part number I-120-H, or gratings for 200 nm to 635 nm or 200 nm to 1000 nm, available from Ocean Optics, Dunedin, FL, part number #10, or part number #13.

Detector 22 is interfaced to a data acquisition computer 60. The array detector is used to collect the response of separation profiles as a function of time. The detector collects data which is processed through process 100 to give a resolved electropherogram showing components x, y, and z. Referring to FIGS. 3B and 3C, data are collected at fixed intervals of time (e.g., $t=0, t=t_z, \ldots, t=t_n$). The data are saved in the computer memory as a data set. After collection of a series of data, each data set is processed as shown and described in FIGS. 1A–1C. For better resolution, a Fourier transform can be applied to data sets.

In general, various kinds of data can be analyzed to determine the Fourier transform of a list of values. In simplest form, the Fourier transform $b_s$ of data set list of $(a_r)$ of length n is taken as:

$$\frac{1}{\sqrt{n}} \sum_{r=1}^{n} a_r e^{2\pi i (r-1)(s-1)/n}$$

See "Mathematica," $2^{nd}$ edition, Stephen Wolfram, page 679, Addison-Wesley Publishing Company, 1991. The Fourier transform can be applied to the data set to more accurately define peaks by their position and area, especially in regions where peaks overlap in the electropherogram.

The convolution operation on the electropherogram with an appropriate weight function can help increase either resolution or sensitivity. Peak resolving in the electropherogram is a result of mathematical properties of convolution and Fourier transformation. Normally, a convolution function in the spatial domain is called a kernel; a pointwise multiplication function in the frequency domain is a filter. A convolution can be carried out by multiplying the Fourier transform of data by the Fourier transform of the kernel and taking the inverse Fourier transform of the resulting product.

A convolution operation $k_{fg}(t)$ is normally denoted by the symbol ⊛. It is a multiplication of one of the functions (e.g., g(t)), with the shifted value f(t-τ) of the other function and the integration of the product over τ, as shown in the following equation:

$$k_{fg}(t) = g(t) \otimes f(t) \int_{-\infty}^{\infty} g(\tau)f(t-\tau)d\tau$$

Mathematically, it can be demonstrated that the Fourier transformation of the convolution of two functions is the product of the transformed functions (See, "NMR Spectroscopy," Vol. 1, CRC Press, Inc., Boca Raton, FL, 1983, at page 173), as shown in the following equation:

$$\mathcal{F}[f(t) \otimes g(t)] = f(v)g(v)$$

Convolution in one domain is equivalent to multiplication in the other domain.

The Fourier transform procedure can be used to help resolve the peaks in the electropherogram. All the sequential steps that are required to sharpen the peaks in the electropherogram can be accomplished using commercially available software (Mathematica or Galactic Software products). Alternatively, digital signal processing chips can be used as a high pass fast Fourier transform (FFT) filter that is applied to the data. These chips can be employed in the present sensor.

A Bessel smoothing function can be applied to the data to minimize the noise in the Fourier-self deconvoluted electropherogram according to the formula:

$$\left[1 - \left(\frac{x}{X}\right)^2\right]^2$$

where $0 \leq x \leq X$ and X is an array (i.e., data set) and where x is normalized between 0 and 1. See, P. R. Griffiths and G. Pariente, *Trends in Analytical Chemistry*, 5:8 (1986). Unlike a boxcar smoothing function (i.e., in which the value goes to zero instantaneously), the Bessel smoothing filter provides a smooth roll-off (i.e., in which the value drops continuously to zero).

The data set can be processed by FT and/or PCA analysis, separately from or in combination with the subtraction process. PCA analysis is described, for example, in Haaland, et al., *Anal. Chem.*, 60: 1193–1201 (1988). FT analysis is described, for example, in Arfken, "Mathematical Methods for Physicists," 3rd edition, Chapters 14 and 15, Academic Press, 1985. The resolution in the FT-chromatogram depends upon the number of data points collected by the array detector during the analysis run. The incremental sampling time is on the order of milliseconds (e.g., between 1 ms and 1000 ms).

Figure 4A:
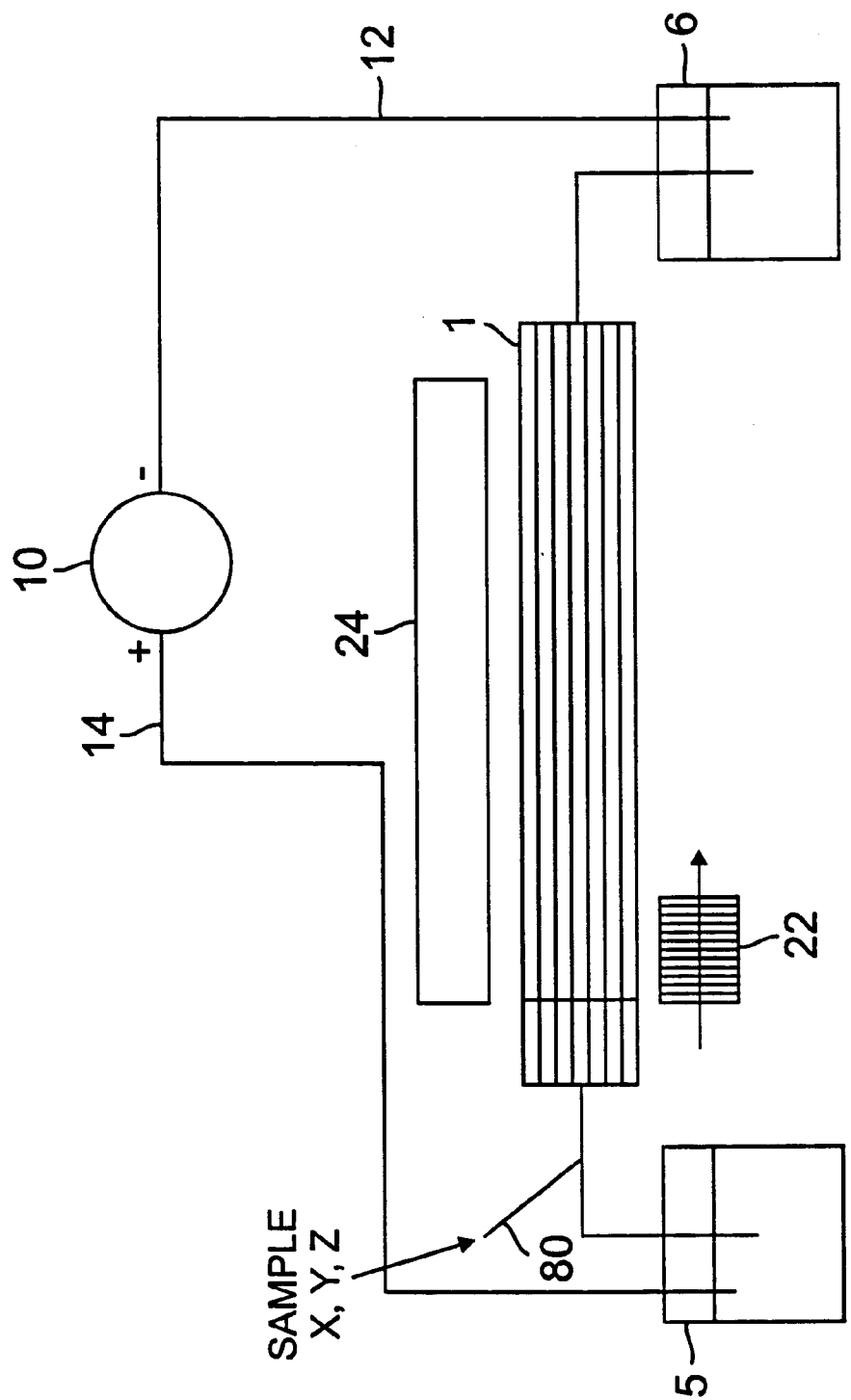
FIG. 4A is a schematic diagram depicting a CZE sensor having a moving detector.

In another possible configuration for FT-CZE, a detector can be used and its position can be moved linearly to follow the separation profile in the capillary. Referring to FIG. 4A, for example, a CZE sensor features fused silica capillary 1 immersed in a buffer solution contained in reservoirs 5 and 6. The sample (containing components x, y, and z) is injected via capillary 80 by, for example, electrokinetic injection. A voltage is applied across the length of capillary 1 using power supply 10 via conductors 12 and 14.

Detector 22 is an variable position array detector, which is illuminated by light source 24 (e.g., mercury, tungsten, deuterium, or zinc lamps). Light source 24 can illuminate the entire detection length of capillary 1 or can move in concert with detector 22. Detector 22 is interfaced to a data acquisition computer 60. The detector is used to collect the response of separation profiles as a function of time which are processed through process 100 to give a resolved electropherogram.

Figure 4C:
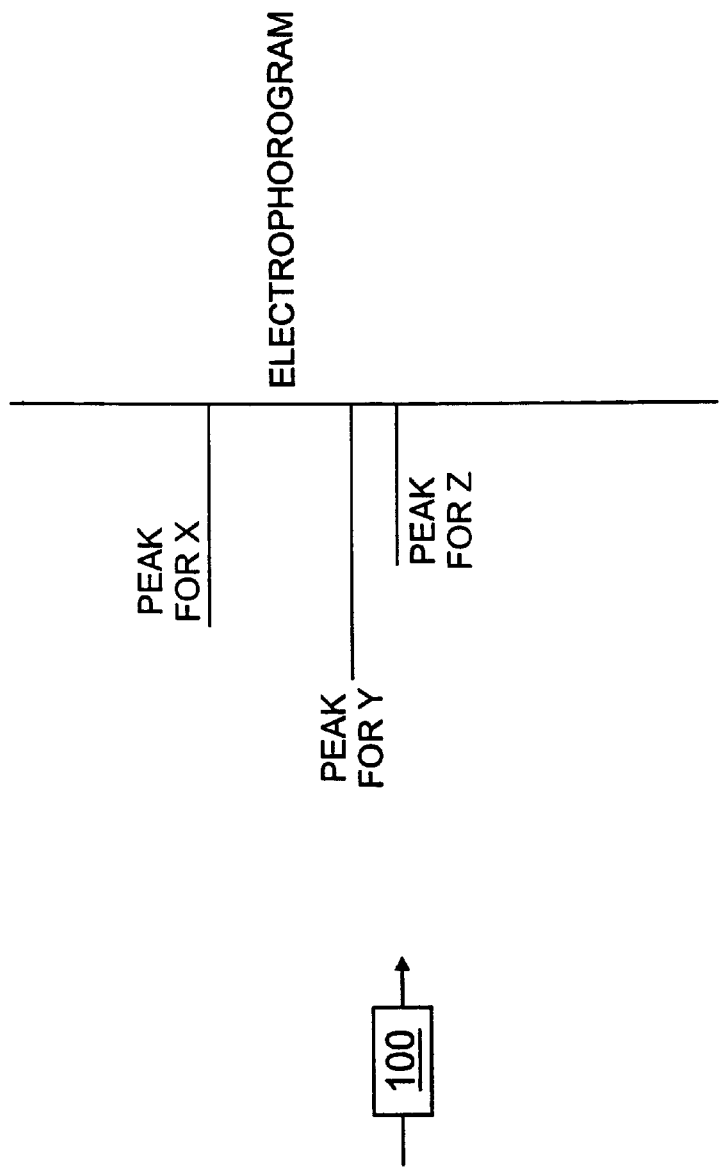
FIG. 4C is an electropherogram (chromatogram) resulting from the graph of FIG. 4B.
Figure 4B:
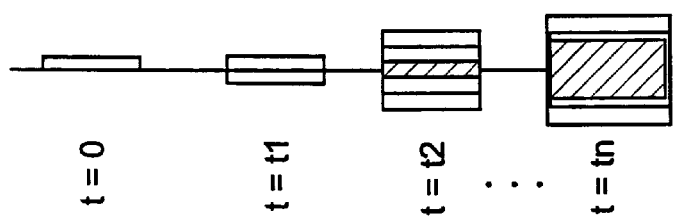
FIG. 4B is a graph showing the absorbance response of the detector of FIG. 4A.

The response from the detector, in the frame of reference of the detector, can be visualized as shown in FIGS. 4B and 4C, assuming that the velocities of the separation profile of the CZE and detectors are the same. Any offset between the two velocities can be corrected. An electronic circuit with a feed back mechanism can be incorporated so that the separation profile and detectors have the same velocities. Subtraction and fast Fourier transform self-deconvolution (FFT) filter techniques can be employed to present the electropherogram with resolved peaks.

In either case, the capillary is not covered with protecting materials. For sensors based on FT-CZE, the length of the capillary is very short (5–10 cm). The short capillary length can be limited by the size of the detector. It is also feasible, in FT-CZE, to vary the applied voltage in incremental steps to monitor the changes in separation profiles.

CZE

CZE is based on the principle that different ions, subjected to a voltage drop along the length of the capillary, migrate through a capillary filled with an electrolyte buffer at different rates. High voltages applied across the length of the capillary (e.g., 100 to 500 V/cm) generate electroosmotic flow that moves the analyte through the capillary. Electrophoresis is performed in narrow-bore, fused silica capillaries which also serve as detector windows. Traditional CZE methods allow one to separate, identify, and analyze all solutes in a solution, however, under most circumstances the analysis time ranges from several minutes to about 30 minutes.

Once the sample is injected, the voltage is applied to the buffer reservoirs where capillary ends are immersed, creating electroosmotic flow. As the mixture travels through the capillary, the different analytes separate. Ideally, once they have separated completely, an analyte travels past the detector assembly, changing the absorbance of light monitored by the detector. The detector can be a diode array detector or any other absorbance detector capable of monitoring a single or multiple wavelengths simultaneously. The response is recorded by the interfaced computer system.

Ideally, there is a linear relationship between absorbance of the solution and component concentrations. Thus, by using calibration standards, the component concentrations of unknown samples can be determined. CZE can be used to detect major and minor components down to the parts-per-billion level (ppb).

The migration and separation of the ions depends on numerous factors, including capillary length ($L_T$), effective capillary length ($L_D$), inner diameter of the capillary (i.d.), electrolytic buffer composition, applied voltage, capillary surface chemistry, and temperature. The buffer composition also affects the separation efficiency of the CZE sensor. Important buffer characteristics include the pH, ionic strength, dielectric constant, viscosity, and the existence of any additional modifiers (e.g., other organic and/or ionic additives).

By applying the method of the invention to CZE, the change in absorbance registered by the detector is processed and projected forward in time (if necessary) to create an electropherogram to quantify the components in the sample mixture. For example, it is possible to identify most water components in 1 to 45 seconds.

CZE Sensor

Referring to FIG. 5A, a CZE sensor features fused silica capillary 1 that is filled with a buffer solution. The capillary can be used for water analysis and is designed to achieve the best resolution in the shortest amount of analysis time. The capillary has an inner diameter (i.d.) between 30 and 100 $\mu$m, most preferably between 50 and 100 $\mu$m, and an effective length of between 0.5 and 30 cm, most preferably less than 15 cm. The capillary serves, at least in part, as a detection window, the dimensions of which depend on the detector used in the sensor. The inside of the capillary can be coated, e.g., with hydrophobic or hydrophilic surface treatments, or can be uncoated. Capillary columns can be purchased from, for example, SGE Incorporated, Austin, TX, J&W Scientific, Folsom, CA, or Polymicro Technologies, Inc., Phoenix, AZ. The temperature of the sampling compartment containing the capillary and buffer reservoir can be maintained at a constant temperature using a thermoelectric cooling mechanism to achieve reproducible migration times.

The ends of the capillary are immersed in a buffer solution contained in buffer reservoirs 5 and 6. Initially, the fluid levels (i.e., buffer solutions) in reservoir 5 and drain reservoir 6 are equal.

A voltage is applied across the length of capillary 1 using power supply 10, which contacts source reservoir 5 via conductor 12. The applied voltage depends on the length of the capillary. The applied voltage per centimeter is preferably between 100 and 500 V/cm. High voltage power supplies are available, for example, from Gamma High Voltage Research Inc., Ormond Beach, FL, such as models MC-100R for 10,000 volts with 100 $\mu$A and MC-50R for 5,000 volts with 200 $\mu$A. Reservoir 6 is grounded by conductor 14. The conductors are composed of inert metal (e.g., platinum) at the point of contact with the buffer solution in the capillary. The high voltage power source for the CZE set-up is typically a 30 kV, 8 $\mu$A power source, e.g., a TR series power supply manufactured by Gamma High Voltage Research, Ormond Beach, FL, or a Spellman power supply model RHR30PN30/ET/RVC manufactured by Spellman High Voltage Electronics Corporation, Plainview, NY. Other known components can be used to make the capillary zone electrophoresis portion of the CZE sensor.

The fused silica capillary is typically preconditioned, for example, by filling the capillary with 0.1 N aqueous NaOH, soaking it for a period of time (e.g., 30 minutes to 3 hours), flushing the capillary with the appropriate buffer, and soaking for an additional 30 minutes. Periodically, the capillary is re-conditioned with a buffer solution and, if necessary, with a base.

Detector assembly 20 monitors the change in light absorbance within the capillary. Detector assembly 20 can be a modified HPLC differential absorbance detector, e.g., the Model 440 manufactured by Waters. Preferably, the detector is a diode array detector, such as a CCD detector for UV/Visible range (190–1080 nm range), available from Princeton Instruments, Trenton, NJ as Dual Diode Array Detector, Model Number RL1024RAQ with dual 1024 diodes, Model Number RL1024SAQ with dual 1024 diodes, or CCD Detector, Model Number RTE/CCD-128. The detector assembly operates by illuminating the detection window with light source 24, e.g., mercury or zinc lamps, or deuterium and monitoring the absorbance change relative to a reference at a particular wavelength(s) using a detector 22, e.g., a photodiode and wavelength filter or, preferably, a diode array, positioned along the detection window. For example, the detector monitors absorbance changes between 200 nm and to the visible range, e.g., 214 nm and 254 nm. The optimal monitoring wavelength depends on the buffer solution composition during indirect analysis. The optimal monitoring wavelength during direct analysis depends on the species being monitored and buffer concentration. When detector 22 is a diode array detector, it is capable of monitoring multiple wavelengths simultaneously. Other detectors that can monitor the change in light absorbance in the capillary can also be used.

The sample can be injected into capillary 1 by electrokinetic injection, which is controlled, in part, by the application of an electrical potential across interface junction 30 by conductor 16. The magnitude and duration of the electric field determines the volume of the injected sample. Alternatively, hydrodynamic injection methods can be employed. Interface junction 30 is a three-way junction of three pieces of capillary column leading to analysis capillary 1, reservoir 5, and microinfusion pump 40.

The microinfusion pump 40 can deliver the analyte solutions to interface junction 30, and controls the delivery to capillary 1 of the water sample from water sampler 50, samples of standard reference solutions 45, and buffer solution from reservoir 7. The various samples are pre-measured volume in, for example, injection loop 35 (e.g., 60 nL). Water sampler 50 gathers the water sample for injection.

In an alternative embodiment, a simple mechanism for adding aqueous sample or buffer solution can eliminate the need for injection and microinfusion pump. Referring to FIG. 5B, reservoir 5 can be used to deliver the sample and then the buffer solution to capillary 1. Capillary 1 and conductor 12 contact the liquid in reservoir 5. Reservoir 5 can contain a few controlled drops of liquid, (e.g., about 0.1 mL) and has a valve mechanism at the bottom. Conduit 62 delivers sample or buffer solution to reservoir 5. At any given time it can contain either buffer solution or the aqueous sample for electrokinetic injection or hydrodynamic injection. Plunger 70 can be pushed inward, releasing a seal between orifice 72 and sealing ball 74 and allowing reservoir 5 to drain so that the solution in the reservoir can be changed. The closing and opening of the valve mechanism can be controlled by the operator or by the computer system.

For the analysis of an aqueous sample, the following steps can be executed by the computer system: (i) push plunger 70 inward for about 10 seconds to drain the contents of reservoir 5; (ii) release plunger 70 to close the bottom of reservoir 5; (iii) allow the sample (i.e., a known volume) to flow through conduit 62 into reservoir 5; (iv) inject the sample by electrokinetic or hydrodynamic injection; (v) push plunger 70 inward to drain the sample from reservoir 5; (vi) release plunger 70 to close the bottom of reservoir 5; (vii) allow the buffer to flow through conduit 62 to fill reservoir 5; and (viii) commence the electrophoretic procedure. The steps are repeated for each sample. The reservoir shown in FIG. 5B can be used in place of junction 30 and can simplify the injection procedure.

The detector 22 is interfaced, for example, to an appropriate analog-to-digital board for data acquisition using computer 60 (e.g., an on-board central processing unit with integrating capabilities, or a personal computer). The data can be processed using LabCalc software Version 2.2, available from Galactic Industries, Mathematica Version 3.0, available from Wolfram Research, or MathCad plus 6.0 from MathSoft, Cambridge, MA. Computer 60 can also control sample acquisition and sample injection. Computer 60 also coordinates running of reference samples and calibration samples and can be used to analyze the time-dependant electrophoretic data.

The anion buffer solution, which is used to analyze anions, has a sodium chromate concentration of between 1.0 and 10.0 mM, e.g., between 3.0 and 6.0 mM (e.g., 5.0 mM), in distilled, deionized water. The anion buffer solution can also contain cesium bromide as an internal standard, at a concentration of between 0.01 and 1.0 mM, e.g., between 0.2 and 0.6 mM (e.g., 0.4 mM). The pH of the solution is adjusted to between 7.0 and 9.0, e.g., between 7.5 and 8.5 (e.g., 8.1), by the addition of dilute aqueous sulfuric acid. Other chromate salts (i.e., potassium chromate, sodium dichromate and potassium dichromate) and bromide salts can be used in the anion buffer solution.

The cation buffer solution, used to analyze cations, is an aqueous solution containing imidazole at a concentration between 1.0 and 10.0 mM, e.g., between 2.0 and 7.0 mM (e.g., 5.0 mM), and 18-crown-6 ether at a concentration between 1.0 and 20.0 mM, e.g., between 5.0 and 10.0 mM (e.g., 7.4 mM), in distilled, deionized water. The 18-crown-6 ether is a chelating agent that assists in separating cation components. More specifically, 18-crown-6 ether chelates potassium. Other chelating agents specific for other metal ions can be used. The pH of the solution was adjusted to between 2.0 and 6.0, e.g., between 3.0 and 5.0 (e.g., 4.6), by the addition of dilute aqueous sulfuric acid. A barium salt (e.g., barium sulfate) can be added at a concentration between 10 and 100 ppm (e.g., 61 ppm) as an internal standard. Other aromatic nitrogen-containing bases can be used in the cation buffer solution.

Electrokinetic injection can be used to introduce the sample into the capillary. Electrokinetic injection is controlled by the magnitude and duration of an electric field applied across the injection interface. For example, a 3 kV field can be applied over the injection region for between 0.1 and 5 seconds (e.g., 1 second). Alternatively, the sample can be injected hydrodynamically by applying a pressure differential at the end of the capillary farthest from the detector. One way to achieve injection is to raise the capillary end to a height of 10 cm for longer capillaries, immerse the end in the sample for 1 to 5 seconds (e.g, 2 seconds), and return the end to the source reservoir. Alternatively a positive pressure in the millibar range (e.g., 100 mbar) can be applied to the surface of the sample in the liquid holder 5 for 1 to 5 seconds.

The CZE sensor is calibrated using solutions with known concentrations of aqueous species. The calibration solutions can include more than one type of species. The instrument is calibrated using samples of varying ionic concentrations that are analyzed and the areas of the resulting electrophoretic peaks are used to create calibration curves. By including an internal standard in the sample (e.g., bromide or barium), an internal check of the internal standard peak position and its area in the electropherogram can be used to determine whether the instrument needs to be recalibrated. Similarly, a quality control check can be implemented where a calibration solution is analyzed periodically (e.g., once every ten test runs). If the results are not consistent with the known concentrations in the calibration solution, the instrument can be recalibrated again.

Analysis of a water sample for contaminants yields an electropherogram depicting the components of the solution. The peak generated for each species is proportional to the concentration of the species in the analysis solution.

The CZE sensor described above can be incorporated into a water analysis system. Such a system includes a water sampler for obtaining water samples, and an analysis system that uses the CZE sensor to determine contaminant levels in the water sample or aqueous extracts from other sources like soil, contaminated soil, chemical products, or other products.

Inside the water analyzer, the microinfusion pump delivers standard solutions to each capillary, establishing calibration curves for the sensor. The water sampler transfers the aqueous sample to the microinfusion pump which prepares the sample for injection, for example, by adding a known amount of an internal standard. The sample is delivered to the analysis capillary by electrokinetic or hydrodynamic injection. The sensor applies a voltage across the capillary for up to 45 seconds, and within this time, all analytes of interest pass the detector assembly.

As each component of the sample passes the detector assembly, the computer records the response of the detector to generate the electropherogram. The computer also determines the concentrations of components in each sample from the peak areas in the electropherogram and the previously established calibration curves, or using multivariant algorithms such as principle component regression (PCA) analysis, Fourier transform analysis (FT), or difference analysis.

Figure 6:
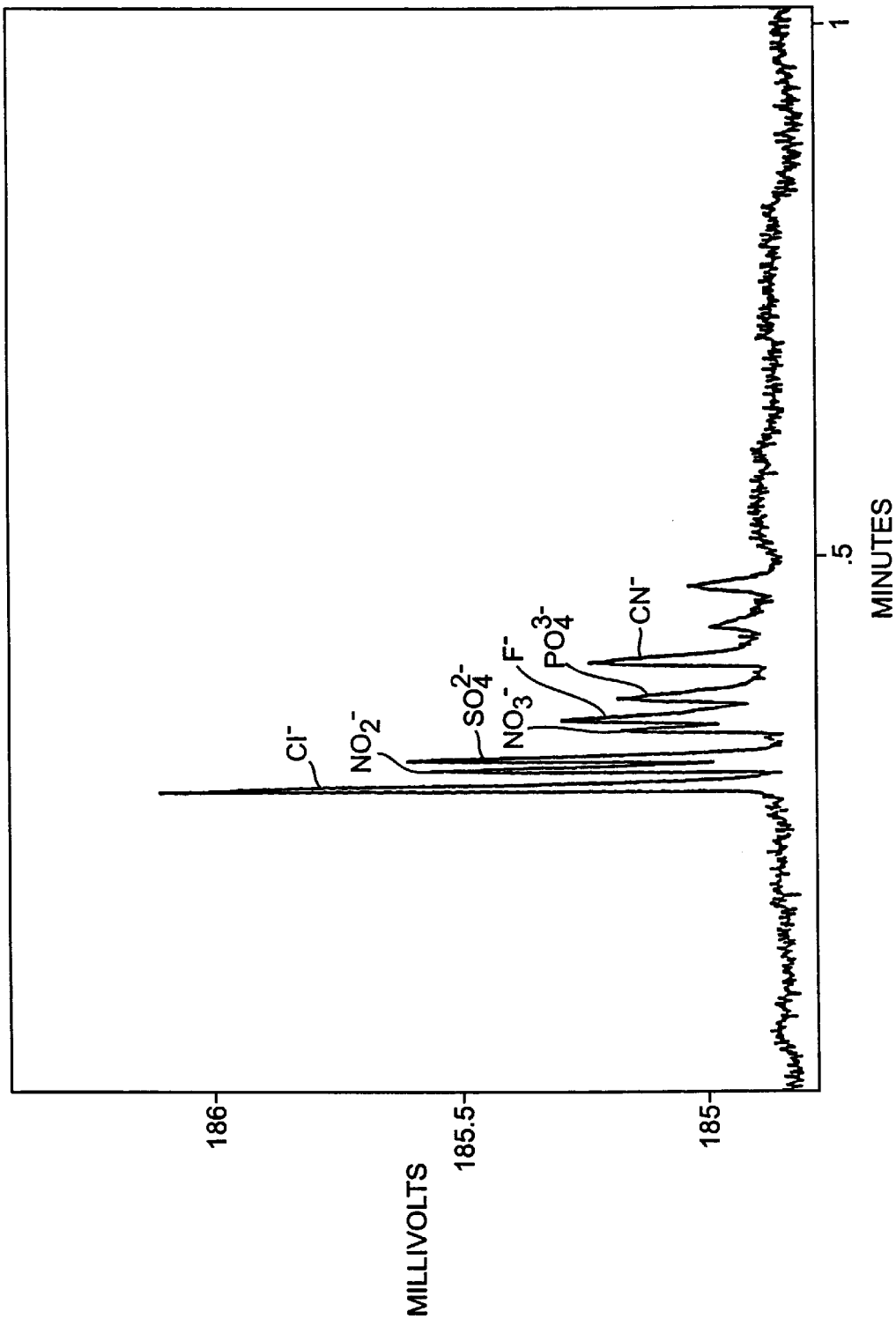
FIG. 6 is an electropherogram showing rapid separation of anionic components in aqueous solution using a CZE sensor.

In an example, FIG. 6 shows an electropherogram displaying the resolution of anionic components in an aqueous solution identified in less than thirty seconds using the CZE sensor described above. The buffer contained 5.0 mM chromate and 2.7 mM cetyltrimethylammonium bromide, the sample was injected electrokinetically (0.5 kV, 2 seconds), and 5 kV were applied to the capillary column ($L_t$=12 cm) during the analysis. The sample contained chloride (110 ppb), nitrite (140 ppb), sulfate (126 ppb), nitrate (100 ppb), fluoride (110 ppb), phosphate (480 ppb), and cyanide (110 ppb). The concentrations were determined by principle component regression analysis.

Figure 7:
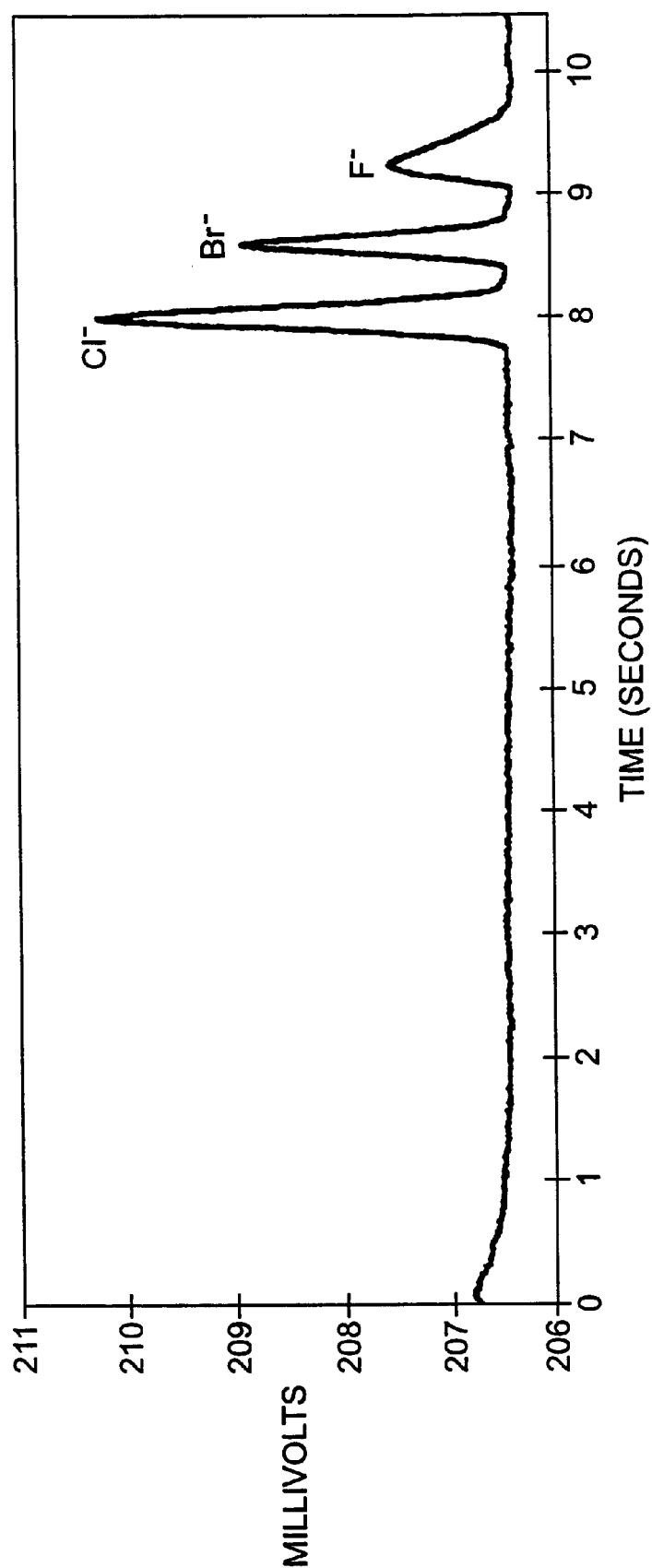
FIG. 7 is an electropherogram showing rapid separation of anionic components in aqueous solution using a CZE sensor.

A fast analysis of anions involving chloride, bromide, and fluoride has also accomplished in less than 10 seconds. These results are shown in FIG. 7 where in aqueous sample containing 1 ppm chloride, bromide, and fluoride was separated using a 49 micron i.d., capillary column ($L_d$=8.7 cm, $L_t$=13.3 cm). The buffer contained 4.4 mM sodium chromate and 3.5 mM (etyl trimethylammonium bromide and had a pH adjusted to 8.1. The sample was injected electrokinetically (0.5 kV, 2 seconds) and field of 750 V/cm was applied across the capillary column.

Figure 8:
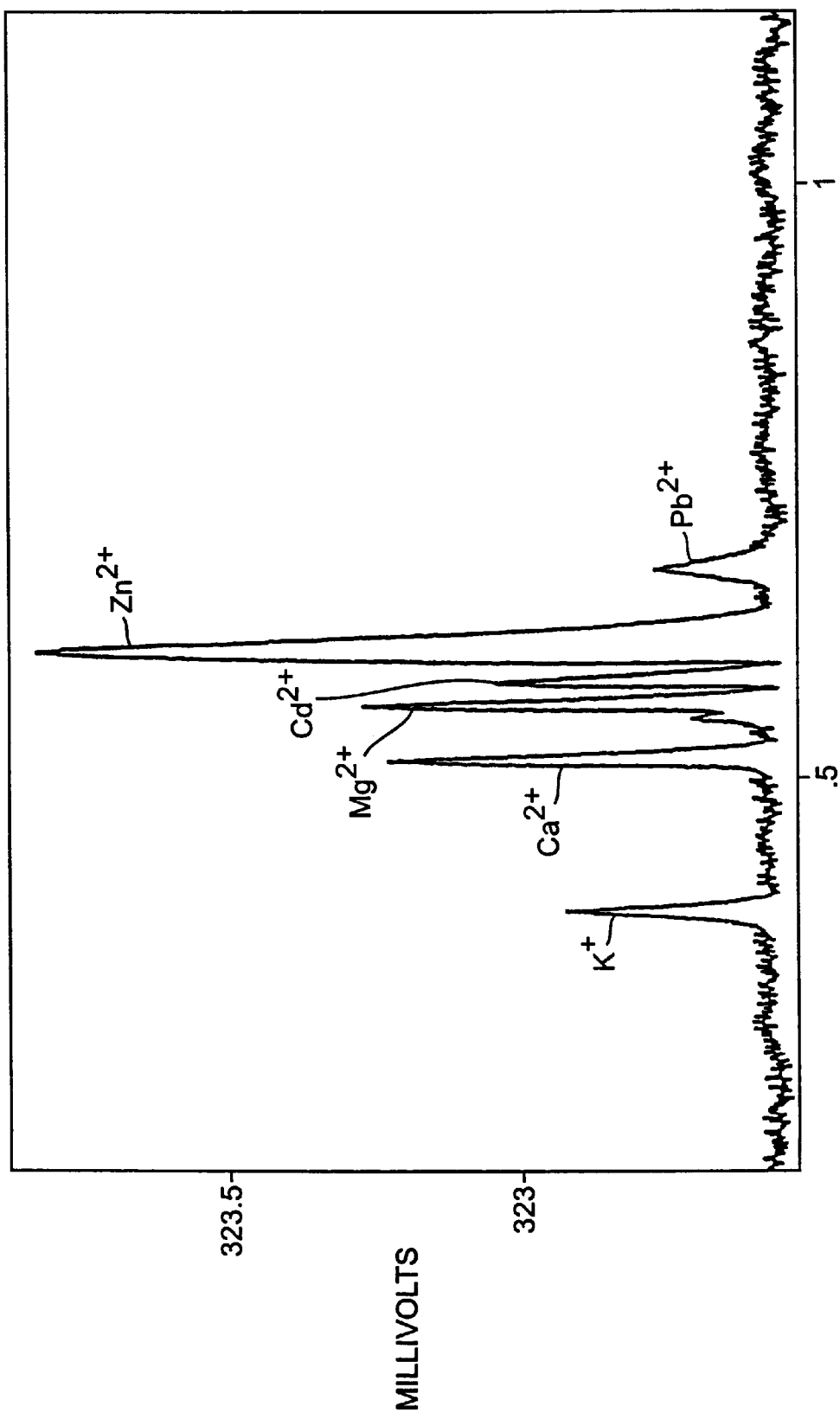
FIG. 8 is an electropherogram showing rapid separation of cationic components in an aqueous solution using a CZE sensor.

In another example, FIG. 8 shows an electropherogram displaying the resolution of cationic components in an aqueous solution identified in less than forty-five seconds using the CZE sensor. The buffer contained 3.6 mM imidazole and 7.2 mM 18-crown-6 ether and had a pH of 3.85. The sample was injected electrokinetically (0.5 kV, 3 seconds), and 5 kV were applied to the capillary column ($L_t$=12 cm, $L_d$=8.3–8.5 cm) during the analysis. The sample contained potassium (280 ppb), calcium (377 ppb), magnesium (245 ppb), cadmium (970 ppb), zinc (229 ppb), and lead (42 ppm) ions. Lead ion detection was limited due to the high absorbance of lead ion at the detection wavelength of 214 nm. It is possible to detect lead at much lower concentrations with improved detectability using suitable sensor configurations (e.g., using high sensitivity detector and an optimal wavelength for indirect detection). The concentrations were determined by principle component regression analysis.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A method of measuring concentrations of individual species in a sample, the method comprising:

introducing a sample containing a plurality of individual species into a capillary associated with a detector arranged to detect each of the individual species in the capillary along an analysis length of the capillary;

moving the sample through the capillary for an analysis time to begin separating the individual species in the sample;

measuring a series of profiles of the plurality of individual species along the analysis length of the capillary at incremental sampling times with the detector during the analysis time to provide a data set;

subtracting each profile from the profile measured one sampling time earlier in the data set to obtain a time dependent data set;

projecting the time dependent data set to obtain a separated concentration profile; and analyzing the separated concentration profile to determine concentrations of individual species in the sample.

2. The method of claim 1, wherein the detector is an absorbance measuring detection device or an array that detects species along the analysis length of the capillary.

3. The method of claim 1, wherein the detector moves along the analysis length of the capillary.

4. The method of claim 3, wherein moving the sample through the capillary comprises applying a voltage across a length of the capillary.

5. The method of claim 4, wherein the applied voltage is varied.

6. The method of claim 1, further comprising applying a time reference shift to each profile in the data set prior to the subtracting step.

7. The method of claim 1, wherein projecting the time dependent data set comprises applying a Fourier transform to the time dependent data set.

8. The method of claim 1, wherein analyzing the separated concentration profile comprises using principle component regression.

9. A method of measuring concentrations of individual species in a sample, the method comprising:

introducing a sample containing a plurality of individual species into a capillary column associated with a detector arranged to detect each of the individual species in the capillary along an analysis length of the capillary;

moving the sample through the column for an analysis time to separate the individual species in the sample;

measuring a series of profiles of the plurality of individual species along the analysis length of the capillary at incremental sampling times with a detector during the analysis time to provide a data set;

applying a Fourier transform to the data set to obtain a separated concentration profile; and analyzing the separated concentration profile by using principle component regression to determine concentrations of individual species in the sample.

10. The method of claim 9, further comprising subtracting each profile from the profile measured one sampling time earlier in the data set to obtain a time dependent data set.

11. A method of claim 9, wherein the detector is an absorbance measuring detection device or an array that detects species along the analysis length of the capillary.

12. The method of claim 9, wherein the detector moves along the analysis length of the capillary.

13. The method of claim 12, wherein moving the sample through the capillary comprises applying a voltage across a length of the capillary.

14. The method of claim 13, wherein the applied voltage is varied.

15. The system of claim 12, wherein the applied voltage is variable.

16. A sensor for measuring species concentrations in a liquid sample, the sensor comprising:

two reservoirs for containing buffer solution;

a capillary connecting the reservoirs, the capillary having an inner diameter of between 25 and 100 micrometers and an effective length of less than 20 cm;

a detector positioned adjacent to the capillary at a distance from the end of the capillary at one of the reservoirs;

a power supply arranged to apply a voltage along the length of the capillary for between 1 and 45 seconds; and a processor connected to the detector, wherein the processor identifies individual species in the liquid sample by difference and projection, principle component regression, or Fourier transform analysis.

17. The sensor of claim 16, wherein the absorbance detector detects species along the effective length of the capillary.

18. The sensor of claim 16, wherein the detector position is variable.

19. The sensor of claim 16, wherein the applied voltage is variable.

20. The system of claim 11, further comprising a power supply arranged to apply a voltage along the length of the capillary for between 1 and 45 seconds.

21. A system for measuring species concentrations in a liquid sample, the sensor comprising:

two reservoirs for containing buffer solution;

a capillary connecting the reservoirs, the capillary having an inner diameter of between 25 and 100 micrometers and an effective length of less than 20 cm;

a detector positioned adjacent to the capillary at a distance from the end of the capillary at one of the resevoirs;

a power supply arranged to apply a voltage along the length of the capillary for between 1 and 45 seconds; and a processor connected to the detector, wherein the processor identifies individual species in the liquid sample by difference and projection, principle component regression, or Fourier transform analysis.

22. The sensor of claim 21, wherein the absorbance detector detects species along the effective length of the capillary.

23. The sensor of claim 21, wherein the detector position is variable.

24. The sensor of claim 21, wherein the applied voltage is variable.

25. The sensor of claim 21, wherein the liquid sample is substantially aqueous.

* * * * *